United States Patent [19]
Brown

[11] Patent Number: 5,461,844
[45] Date of Patent: * Oct. 31, 1995

[54] METHOD OF USING A NEEDLE SHIELD DEVICE FOR SURGICAL PACKAGES

[75] Inventor: David L. Brown, Wallingford, Conn.

[73] Assignee: United States Surgical Corporation, Norwalk, Conn.

[*] Notice: The portion of the term of this patent subsequent to Aug. 17, 2010, has been disclaimed.

[21] Appl. No.: 279,129

[22] Filed: Jul. 22, 1994

Related U.S. Application Data

[62] Division of Ser. No. 55,959, Apr. 30, 1993, Pat. No. 5,358,102, which is a continuation of Ser. No. 852,686, Mar. 17, 1992, abandoned, which is a continuation-in-part of Ser. No. 636,227, Dec. 31, 1990, Pat. No. 5,236,082.

[51] Int. Cl.⁶ .................................................. B65B 11/58
[52] U.S. Cl. ............................ 53/449; 53/415; 53/430; 53/452
[58] Field of Search ........................... 206/63.3, 363; 53/410, 412, 415, 425, 430, 445, 449, 452, 462

[56] References Cited

U.S. PATENT DOCUMENTS

| | | |
|---|---|---|
| 2,993,589 | 7/1961 | Zoller et al. . |
| 3,136,418 | 6/1964 | Stacy et al. . |
| 3,444,994 | 5/1969 | Kaepernik et al. . |
| 3,726,057 | 4/1973 | Kemble ............................... 53/449 X |
| 3,759,376 | 9/1973 | Lisowski ............................. 53/430 X |
| 3,815,315 | 6/1974 | Glick .................................. 53/449 X |
| 3,857,484 | 12/1974 | Thyen . |
| 3,939,969 | 2/1976 | Miller et al. . |
| 3,959,947 | 6/1976 | Sonnino ............................... 53/430 X |
| 4,063,638 | 12/1977 | Marwood . |
| 4,069,912 | 1/1978 | Black et al. . |
| 4,120,395 | 10/1978 | Mandel et al. . |
| 4,249,656 | 2/1981 | Cerwin et al. . |
| 4,253,563 | 3/1981 | Komarnycky . |
| 4,284,194 | 8/1981 | Flatau . |
| 4,391,365 | 7/1983 | Batchelor . |
| 4,406,363 | 9/1983 | Aday . |
| 4,412,614 | 11/1983 | Ivanov et al. . |
| 4,413,727 | 11/1983 | Cerwin et al. . |
| 4,427,109 | 1/1984 | Roshdy . |
| 4,483,437 | 11/1984 | Cerwin et al. . |
| 4,491,218 | 1/1985 | Aday . |
| 4,496,045 | 1/1985 | Ferguson et al. . |
| 4,555,016 | 11/1985 | Aday et al. . |
| 4,572,363 | 2/1986 | Alpern . |
| 4,574,948 | 3/1986 | Huck et al. . |
| 4,627,223 | 12/1986 | Janhonen ............................. 53/449 |
| 4,708,241 | 11/1987 | Black . |
| 4,884,681 | 12/1989 | Roshdy et al. . |
| 4,896,767 | 1/1990 | Pinheiro . |
| 5,048,678 | 9/1991 | Chambers . |
| 5,078,730 | 1/1992 | Li et al. . |

Primary Examiner—John Sipos
Assistant Examiner—Daniel Moon

[57] ABSTRACT

A method of using a needle shield for retainers enclosing suture-needle assemblies constructed of a fibrous material and foldable about at least two score lines to provide a protective device against needle damage, accidental sticking of the user's fingers, and puncture of the package within which the retainer is packaged.

4 Claims, 9 Drawing Sheets

METHOD OF USING A NEEDLE SHIELD DEVICE FOR SURGICAL PACKAGES

This is a divisional of U.S. application Ser. No. 08/055,959 filed Apr. 30, 1993, now U.S. Pat. No. 5,358,102 which is a continuation of application Ser. No. 07/852,686 filed on Mar. 17, 1992, now abandoned, which is a continuation-in-part of application Ser. No. 07/636,227 filed Dec. 31, 1990, now U.S. Pat. No. 5,236,082.

Background of The Invention

1. Field of the Invention

The present invention relates to surgical suture-needle packages, and more particularly to a needle shield device for protecting the tip of the needles from damage and to eliminate the possibility of accidental sticking of a person's finger by the needles, as well as to prevent puncturing of the sterile package in which the needles are enclosed during storage and handling.

2. Discussion of the Prior Art packaging,devices for needles and suture needle assemblies which include protective flaps or covers are well known in the art. These packages generally include a fold over flap or cover which encloses the needles or the needle tips in the package. In many cases, the flap is integrally formed as part of the package so that the flap or cover comprises a tear away portion which exposes the needles upon opening of the package.

The packaging of sutures, particularly sutures having a needle positioned on at least one end of the suture, requires special consideration to eliminate the possibility of puncturing of the sterile package by the needle enclosed therein, as well as to protect a surgeon or surgical team member from accidental sticking during handling while opening the package. It is also desirable to protect the needles themselves after the package is open against damage to the tips.

Typically, the suture is wound on a retainer prior to enclosure within a sterile, moisture-impervious outer package. The retainer may comprise any containment device, and generally is constructed of a fibrous, somewhat rigid material such as paperboard, pressed paper, or a cardboard material. The retainer may be formed as a series of panels which are foldable over each other to secure the suture between the panels. In most cases, the needles are either loosely positioned between the panels or latched to a panel and folded between the panels with the sutures. Examples of retainers which fold a series of panels over onto themselves to secure the sutures and needles therebetween are disclosed in U.S. Pat. No. 3,136,418 to Stacy et al. and U.S. Pat. No. 3,939,969 to Miller et al.

Another type of suture retainer is constructed as a two piece device having a molded plastic bottom tray which includes a coiled passageway. The suture lays in the passageway, and the entire tray is covered by a top cover or layer of a sheet-like material. When needles are provided on the sutures, the needles are usually secured outside the retainer; that is, the sutures are in the passageway of the bottom tray and covered by the top sheet, while the needles are external to the retainer and must be secured by some additional means. Usually, the needles are positioned in a holding member such as a foam needle park. An example of such a retainer is disclosed in U.S. Pat. No. 3,338,401 to Regan, Jr.

In order to maintain the sterility of such a device, the retainer having the needles attached thereto are further packaged in a moisture-impervious package, constructed of metal foil, plastic film or other suitable materials. A disadvantage to this arrangement lies in the fact that the sharp needles directly rest against the inner surface of the outer package, and may puncture the outer package during storage, handling, etc. This will of course destroy the sterility of the suture and needle assembly, and may expose the surgeon or surgical assistant to a hazard involving accidental sticking.

Several tear away type needle covers for use with surgical suture-needle assembly packages are provided in the prior art. These packages generally comprise a panel having either perforations or score lines which facilitate tearing a portion of the panel from the package to expose the needles after the package is opened. After the tear away cover or flap is removed, the needle and suture assembly may be removed from the package in the conventional manner.

In the prior art, several packages having tear away cover flaps are disclosed, such as U.S. Pat. No. 4,063,638 to Marwood. The package disclosed in Marwood comprises a three panel package, where the suture is wound and held at the center panel and the needle is held in an outer panel. A panel having the tear away flap is provided on the outer panel opposite the needle retaining panel, and the tear away flap is folded over the sutures followed by the needle retaining flap. Upon opening the package, the flap is torn away, thus revealing the needle so that the needle may be removed in the conventional manner.

Another type of package prevalent in the prior art provides a fold over flap which covers the needles within the package. When the package is opened, the fold over flap is unfolded to reveal the needles so that the needles may be removed in the conventional manner. Such a device is disclosed in U.S. Pat. No. 4,574,948 to Huck et al. Huck et al. provides a packaging device in which the suture is secured on one panel of the package and the needles are secured on a second panel. A fold over flap is provided to cover the needles to prevent sticking of the user and to prevent damage to the needle tips. As the package is opened, the fold over flap is unfolded to reveal the needles so that the needles may be removed in a conventional manner. A similar type device is disclosed in U.S. Pat. No. 4,708,241 to Black, deceased.

The devices disclosed in the prior art suffer from several disadvantages in which the risk of accidental sticking of the needle into the fingers of the user is not significantly reduced or eliminated, and further, many of these devices suffer the disadvantage in that the cost of packaging is increased due to the necessity for additional packaging material as well as increasing the number of packaging steps during assembly.

Surgical suture-needle retainers and needle packages are generally constructed of a material which resists folding and bending and which is strong enough to hold a coiled suture in place without the risk of the suture unraveling during shipment. The retainer must also be rigid enough to resist bending or folding to eliminate the risk of creasing the suture during shipment, so that when the retainer is opened the suture may be removed from the package without creases or bends. There is significant emphasis in the surgical suture industry placed on the "memory" retention of the suture material, so that the suture retains its original shape upon removal from the retainer with a minimum of bends and creases, even after extended periods of time within the retainer. In view of this, many of the retainers disclosed above which provide a needle retaining member which is folded over the package increase the amount of bends in the suture material during packaging, which may lead to an undesirable suture-needle assembly upon removal from the retainer.

A further disadvantage of the prior art retainers is that in using the retainer itself to protect the needles, such as those retainers disclosed above having a tear away portion, there is a requirement that additional packaging material must be provided to cover the needle. Given the fact that many of these retainers employ rigid panels, sometimes in laminate form, the cost of packaging is necessarily increased to provide the needle cover. In addition, the step of forming the retainer material must include the addition of score lines or perforations to facilitate the tear feature to expose the needles.

An additional disadvantage to these fold over devices lies in the face that the needles are hidden from view until that portion of the retainer is either torn away or unfolded to reveal the needles. Consequently, the user is at risk of accidentally sticking himself with the needles since he cannot see the needles during the tear away or unfolding step.

The novel needle shield device for surgical retainers and packages having needles or suture-needle assemblies of the present invention obviates the disadvantages encountered in the prior art and provides a universal needle shield device for use with any surgical needle or suture-needle retainer or package. The shield of light weight material and provides the user with protection against sticking while further providing protection for the needle tips against damage. The shield further protects the outer sterile package in which the retainer is enclosed from inadvertent puncture. The needle shield of the present invention may be used with any surgical needle or suture-needle assembly package, and eliminates the requirement for providing additional packaging material and the requirement for complex folding arrangements of the rigid retainer material to cover the needles.

SUMMARY OF THE INVENTION

The present invention provides a novel needle shield device for surgical suture and needle retainers and packages having needles or suture-needle assemblies packaged therein. The device may also be used with syringes or hypodermic-type needles to protect the needle and to guard against sticking during opening of the package, by allowing the user to view the needle during the opening procedure so that the user knows at all times where the sharp tips of the needles are located.

The needle shield of the present invention essentially comprises a sheet of fibrous material which is attachable to a cover panel of the needle or suture-needle assembly retainer in the vicinity of the tips of the needles, and is preferably secured by adhesives, glue or the like.

The needle shield of the present invention has a substantially rectangular shape, and is provided with a series of score lines or fold lines along the edges of the rectangle from which outwardly directed projections extend from the needle shield, and it is at this location that the needle shield is secured to the cover panel of the retainer. Preferably, an adhesive-backed foam needle park or holder is secured across the fork-like projection and then is secured directly to the retainer in the area of the needle tips. The spaces between the fork-like projections allow the adhesive-backed needle park to adhere to the cover panel of the retainer. In this manner, the needles are retained in the needle park so that their tips lie on the fibrous material which forms the needle shield.

Intermediately spaced between the edge having the fork-like projections and the opposite parallel edge, is a scored line which forms a first fold line of the needle shield and which is parallel to the edge forming the forked projections. Preferably, two additional scored fold lines are provided which are perpendicular to the first scored line and the edge of the device having the forked projections. It is these two scored lines, preferably parallel to each other, which form the side edges of the needle shield. Wing-like projections having generally semi-circular or triangular shapes extend outwardly from the scored lines which are folded about the body of the shield in a manner described below.

The retainers with which the needle shield of the present invention is used may be any type of retainer for holding a suture and needle combination, where the needles extend outside the retainer while the suture is secured within. The retainer may comprise a plurality of foldable panels, including a suture winding panel, a bottom panel and a cover panel. In its simplest form, the retainers includes a bottom panel and a cover panel, with the suture positioned between the panels, and the needles located outside the retainer adjacent the cover panel.

In addition the retainer may be of the molded-tray type in which the bottom cover of the retainer is provided with at least one curved passageway which accommodates the suture. A cover panel, which may comprise any sheet-like material such as pressed paper, cardboard, plastic, or spun bonded polyolefin fibers (known as Tyvek, a registered trademark of DuPont), overlies the bottom stay and is secured about its periphery to the bottom tray. The cover panel is preferably provided with at least one aperture through which the sutures extend so that the needles are positioned outside the retainer adjacent the cover panel.

In use, the foam needle park is positioned across the fork projections and the needle shield and foam park are adhered to the cover panel of the retainer adjacent the needles. The needles are then positioned in the needle park so that the tips of the needles lie on the needle shield. The shield is then folded over itself at the first scored line, to wrap the body of the shield about the needle tips. The wing-like projections are then folded along the perpendicular side score lines under the bottom of the sheet to hold the needle shield about the needle tips.

The retainer and needle shield are then inserted into an outer sterile package which may be a metal foil pouch or a so-called "breather-pouch" having a plastic film overlying a Tyvek layer. The needle shield protects the outer package by eliminating the possibility of puncturing of the package due to the shield fully enclosing the sharp-tipped needles. This is important to maintain sterility of the suture-needle assembly, as well as to prevent drying out of the suture, particularly if the suture is a gut-type or collagen-type suture which requires packaging in a conditioning fluid medium to maintain its suppleness.

It is also contemplated that the needle shield be provided with an end guard member which comprises a projection which extends upwardly from the edge of the needle shield opposite the fork projections so that when one of the side wing-like extensions is folded under the needle shield, the fold line extends through this projection so that the shield is wrapped about the suture-needle connection point of the endmost suture-needle assembly, to prevent puncture of the outer package at the butt-end of the needles.

The present invention provides a needle shield which may be used with any type of needle retainer package, whether the needles be for use in a suture-needle assembly, a hypodermic-type syringe needle, or the like. The fibrous material which comprises the needle shield is preferably a material such as Tyvek, which is constructed of polyolefin fibers which are bonded by heat and calendar pressure. While this is the preferred material, other, similar fibrous material such as pressed paper or fiberboard are also contemplated for use as the needle shield of the present invention. The scored fold lines may also be perforated lines which may facilitate easier folding and unfolding.

BRIEF DESCRIPTION OF THE DRAWINGS

The features of the present invention will become more readily apparent and may be understood by referring to the following detailed description of an illustrative embodiment of the needle shield for surgical suture retainers and its novel construction, taken in conjunction with the accompanying drawings in which.

DETAILED DESCRIPTION OF THE PREFERRED EMBODIMENTS

Figure 1:
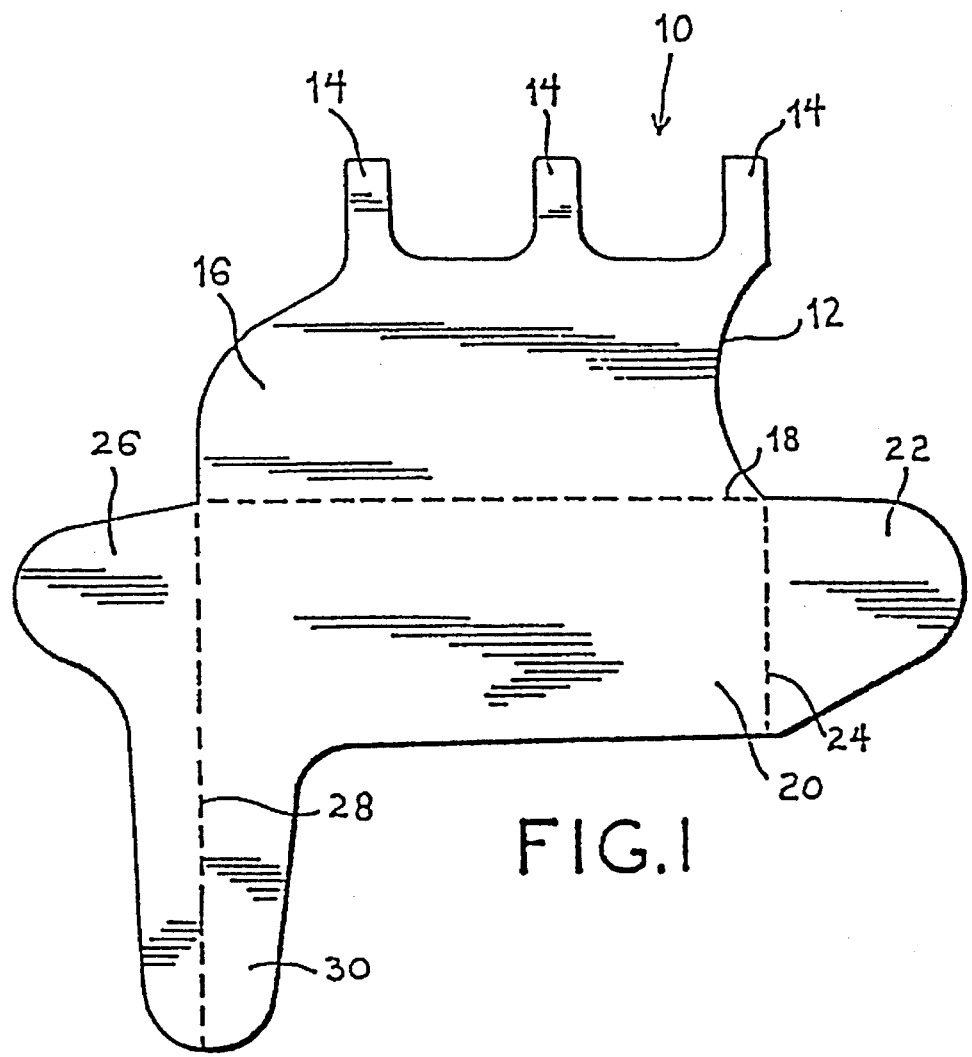
FIG. 1 illustrates a top plan view of a needle shield according the present invention.

Referring now in specific detail to the drawings, in which like reference numerals identify similar or identical elements throughout the several views, FIG. 1 shows the needle shield 10 of the present invention. Needle shield 10 comprises a flat sheet of fibrous material, preferably a non-woven fibrous sheet such as Tyvek which comprises spun bonded polyolefin fibers pressed together to form a sheet of fibrous material. While it is contemplated in the preferred embodiment that needle shield 10 be constructed of Tyvek, it is clear that any fibrous material may satisfy the requirements for protecting packaged needles from damage and eliminating the possibility of accidental sticking of a person's finger by the needles, as well as preventing puncture of the outer packages from the sharp needles.

The body portion 12 of needle shield 10 is provided with a series of fork-like projections 14 which extend outwardly from body 12 and are spaced from each other as shown. A score line 18 is provided on body 12 which essentially separates body 12 into two halves. Bottom half 16 and top half 20 are described in more detail in relation to FIGS. 2 and 3.

Wing-like projections 22 and 26 extend outwardly from body 12 and are further defined by score line 24 which allows projection 22 to be folded onto body 12, and score line 28 which allows projection 26 to be likewise folded. A third projection 30 is provided along the edge of top sheet 20 opposite the edge defined by score line 18. Projection 30 will be described in more detail below in reference to FIGS. 2 and 3.

Figure 2:
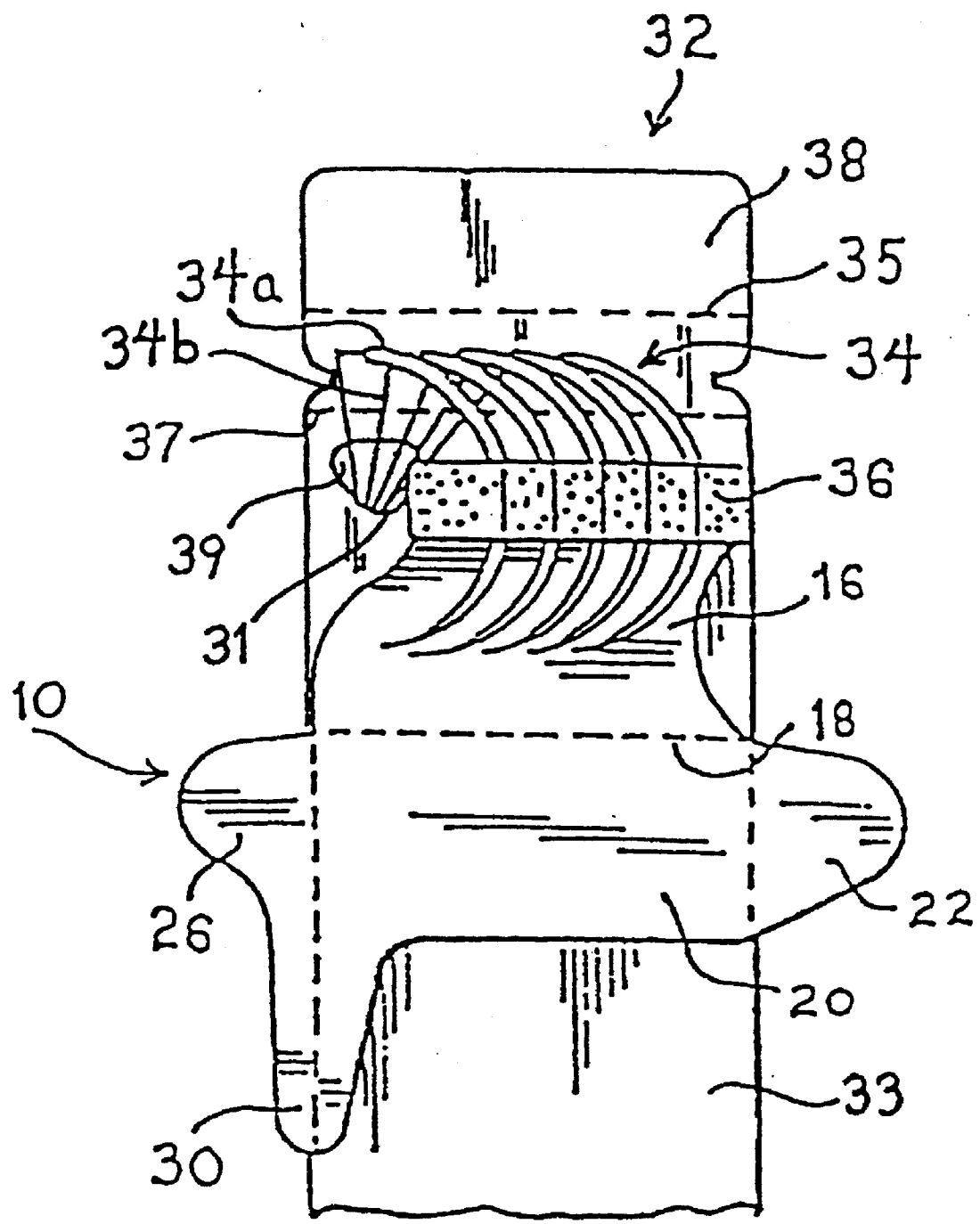
FIG. 2 illustrates the needle shield of FIG. 1 positioned on a suture-needle retainer in the open position to reveal the needles of the retainer.
Figure 10:
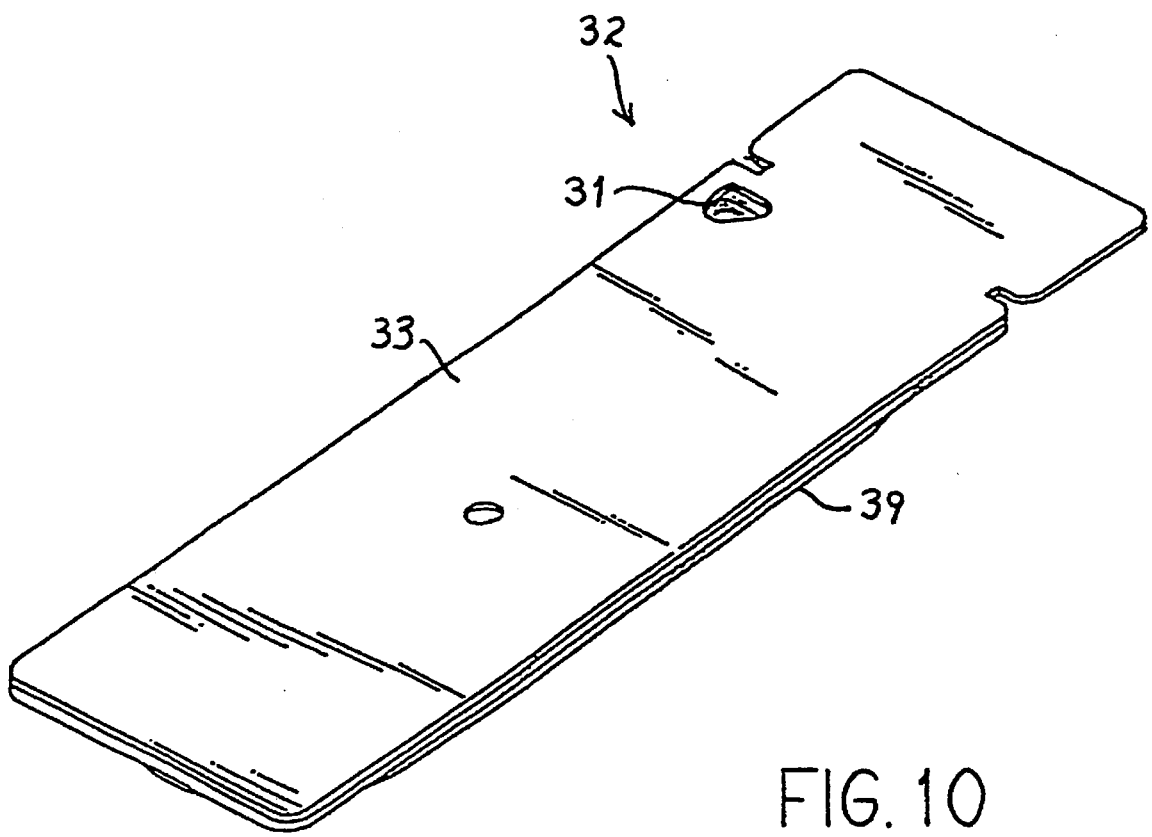
FIG. 10 illustrates a perspective top view of a retainer having the needle shield of the present invention attached thereto.
Figure 10A:
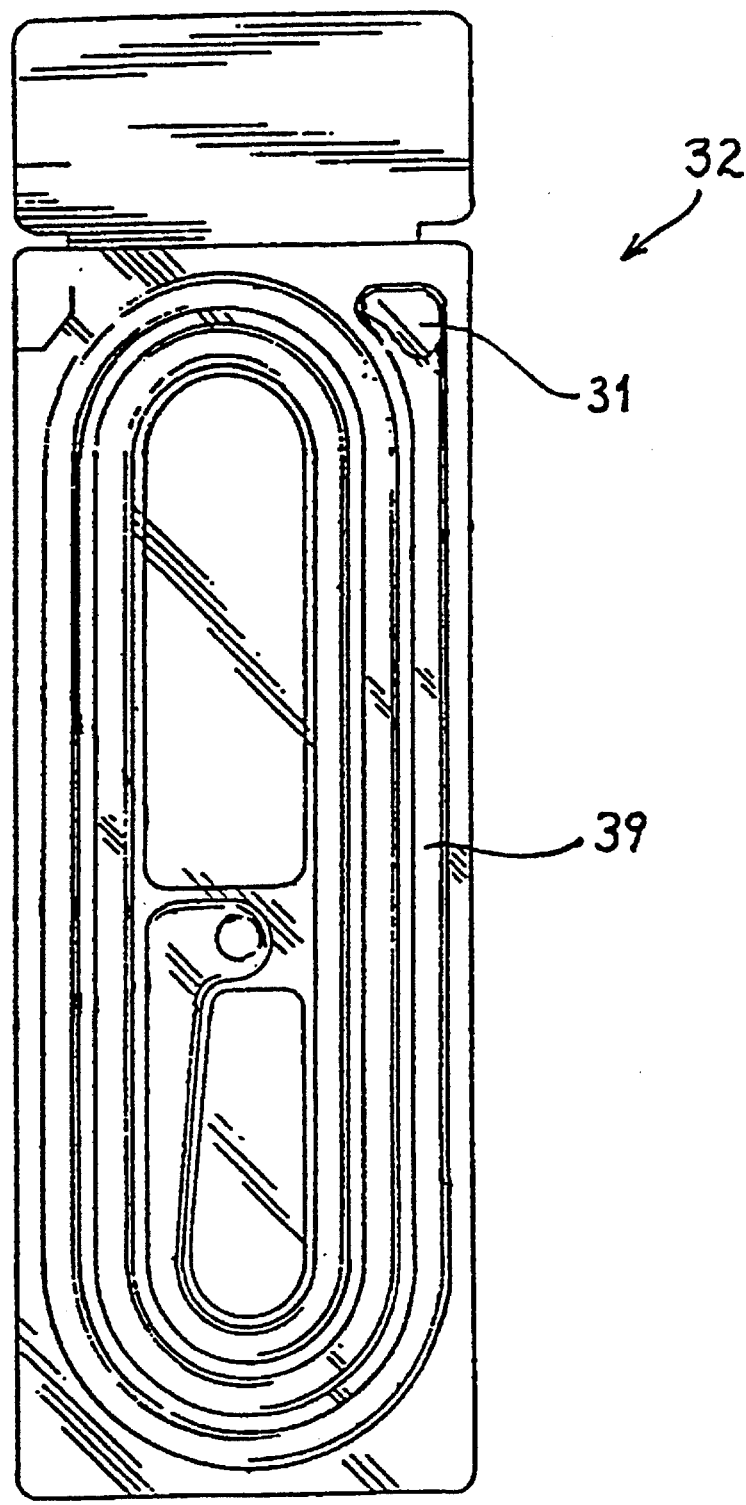
FIG. 10A illustrates a bottom plan view of the retainer of FIG. 10.

Turning now to FIG. 2, a suture-needle retainer 32 is shown having needle shield 10 positioned on cover panel 33. As best seen in FIGS. 10 and 10A, retainer 32 includes top or cover panel 33 and bottom panel 39. Bottom panel 39 may comprise a molded tray having at least one curved passageway molded therein for holding at least one suture. Preferably the curved passageway is arranged in a spiral coil. Top or cover panel 33 comprises a sheet of material, constructed of paper, paperboard, plastic or preferably Tyvek, and is secured about the periphery of bottom panel 39. Cover panel 33 is provided with at least one aperture 31, through which sutures 34b extend so that needles 34a are located outside retainer 32.

Needle shield 10 is preferably secured to cover panel 33 of retainer 32 in the vicinity of needle assemblies 34, so that the tips of the needles rest on bottom sheet 16 as seen in FIG. 2. To secure needle shield 10 to retainer 32, any adhesives or glue materials may be used. However, it is preferred that an adhesive backing needle holding member, such as foam needle park 36 be provided to secure needle shield 10 to cover panel 33 of retainer 32. Needle park 36 is provided with an adhesive backing which secures the needle shield 10 to the back of needle park 36 at projections 14. The spacing between projections 14 allows the needle park to be further secured to cover panel 33 of retainer 32 so that needle shield 10 is secured to the retainer between cover panel 33 and foam needle park 36. Needle park 36 also provides a means for holding the needles 34a in position, which assists needle shield 10 in protecting the tips of the needles from damage and the outer package from puncture, as well as to protect a user from accidental sticking.

Figure 3:
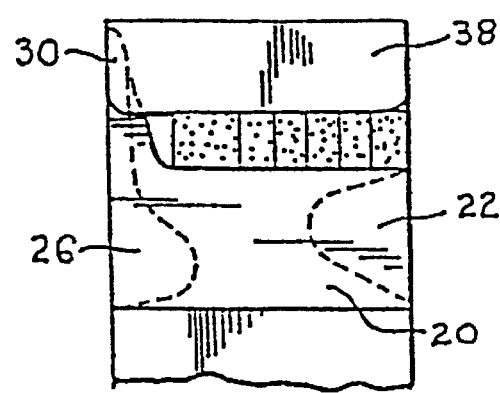
FIG. 3 illustrates the needle shield of FIG. 2 in the closed retainer.

In use, after needle shield 10 has been secured to cover panel 33 of retainer 32 through needle park 36, needles 34a are secured in needle park 36 so that the tips of the needles rest on bottom sheet 16 as shown in FIG. 2. Needle shield 10 is then folded on score line 18 so that top sheet 20 covers the tips of the needles as shown in FIG. 3. Needle shield 10 is so dimensioned that the upper edge of top sheet 20 engages the front edge of needle park 36 to completely enclose the tips of the needles. At this point, wing-like projections 22 and 26 are folded along score lines 24 and 28, respectively, and tucked under bottom sheet 16 to hold needle shield 10 in place. Projection 30 is provided to cover the suture connection to the endmost needle 34a as best seen in FIG. 3. Finally, top flap 38 of suture retainer 32 is folded at perforated line 35 over the suture ends of needle assemblies 34 to completely enclose the needles as shown in FIG. 3. A second perforated line 37 is provided to allow the top flap 38 and upper portion of suture retainer 32 to be folded over in the open position to provided 360° access to the needles 34 from the front or back of the retainer, so that the needles may be removed from either side of the retainer.

Figure 4:
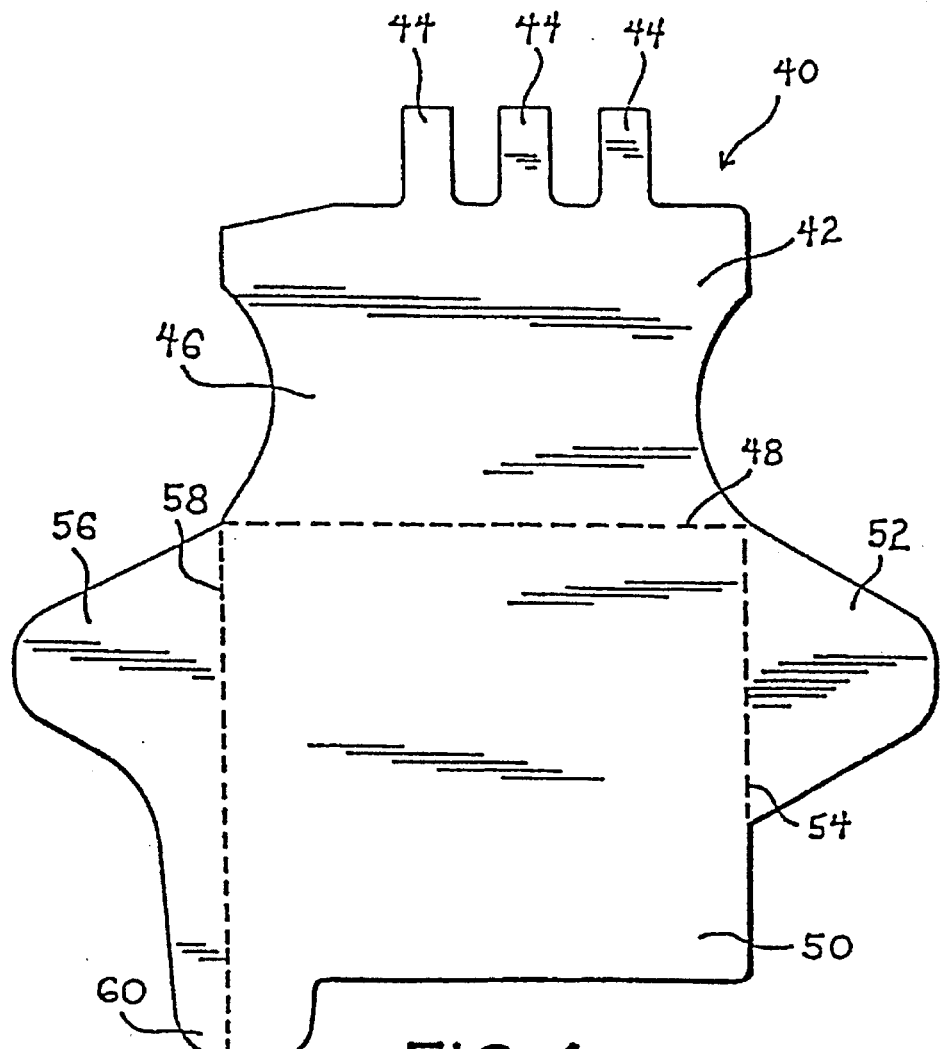
FIG. 4 illustrates a top plan view of an alternate embodiment of the needle shield of the present invention.

Turning now to FIG. 4, needle shield 40 is an alternate embodiment of needle shield 10 of FIG. 1. A sheet of fibrous material 42 is provided having fork-like projections 44 which are spaced from each other as shown. A score line 48 is provided to allow sheet 42 to be folded over itself in much the same manner as shown in relation to FIG. 1. Folding needle shield 40 along score line 48 provides a bottom sheet 46 and a top sheet 50, where top sheet 50 has wing-like projections 52 and 56 which are defined by score lines 54 and 58, respectively. A further projection 60 is provided along the upper edge of top sheet 50 and projection 60 will be described further below in reference to FIGS. 5 and 6.

Figure 5:
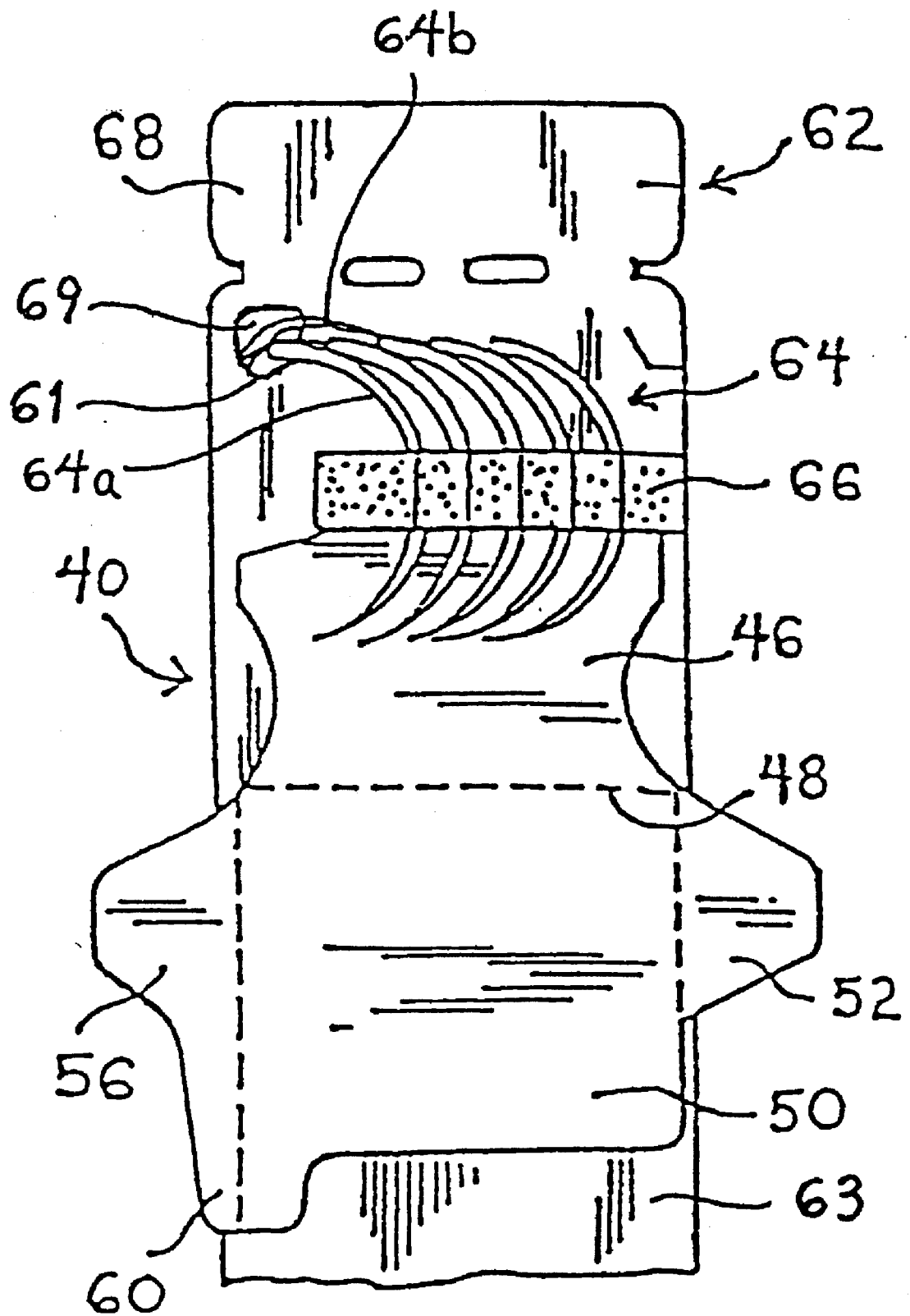
FIG. 5 illustrates the needle shield of FIG. 4 positioned on a suture-needle retainer in the open position.

As best seen in FIG. 5, needle shield 40 is positioned on a cover panel 63 of suture-needle retainer 62 in the vicinity of needles 64. Package 62 is identical to package 32 described above and shown in FIGS. 10 and 10A, and includes top or cover panel 63 and a bottom tray-type panel 69 over which cover panel 63 is secured. Cover panel 63 is provided with at least one aperture 61, so that sutures 64b, positioned between panels 63 and 69, extend through aperture 61 and terminate in needles 64. Needle shield 40 is secured to cover panel 63 of retainer 62 through the provision of an adhesive backed foam needle park 66 which is similar to needle park 36 as shown in FIG. 2. As above, needle shield 40 is secured to cover panel 63 of the retainer between the adhesive backed needle park 66 and the face of cover panel 63, where the needle park 66 secures shield 40 to cover panel 63 to hold fork-like projections 44 in place. Needles 64 are then secured in needle park 66 as seen in FIG. 5.

Figure 6:
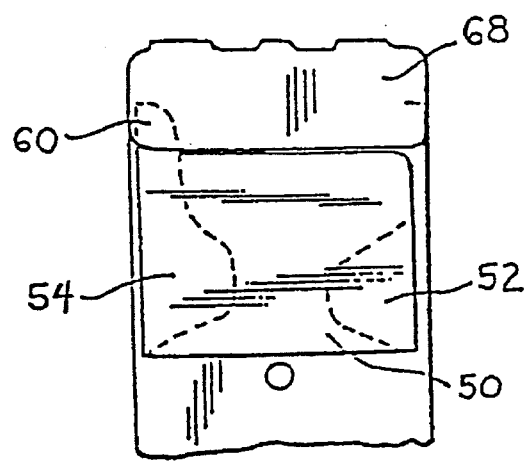
FIG. 6 illustrates the needle shield of FIG. 5 positioned on a suture-needle retainer in the fully closed position.

In use, after the sutures are placed in retainer 62 and extend through aperture 61, needle shield 40 is secured to retainer 62 at cover panel 63. Needles 64 are positioned in needle park 66 so that the tips of needles 64 rest on bottom sheet 46. Needle shield 40 is then folded at score line 48 so that top sheet 50 covers the needle tips which are now positioned between top sheet 50 and bottom sheet 46. As seen in FIG. 6, score line 48 is so positioned that when needle shield 40 is folded at score line 48, the upper edge of top sheet 50 completely covers needle park 66. At this point, wing-like projections 52 and 56 are folded on score lines 54 and 58, respectively, and tucked under bottom sheet 46 to secure the needle shield. As been seen in FIG. 6, upper projection 60 provides a protective cover for the suture end of endmost needle 64a. Finally, top flap 68 of retainer 62 is folded over the suture ends of the needles 64 to completely enclose the needles as shown.

Figure 7:
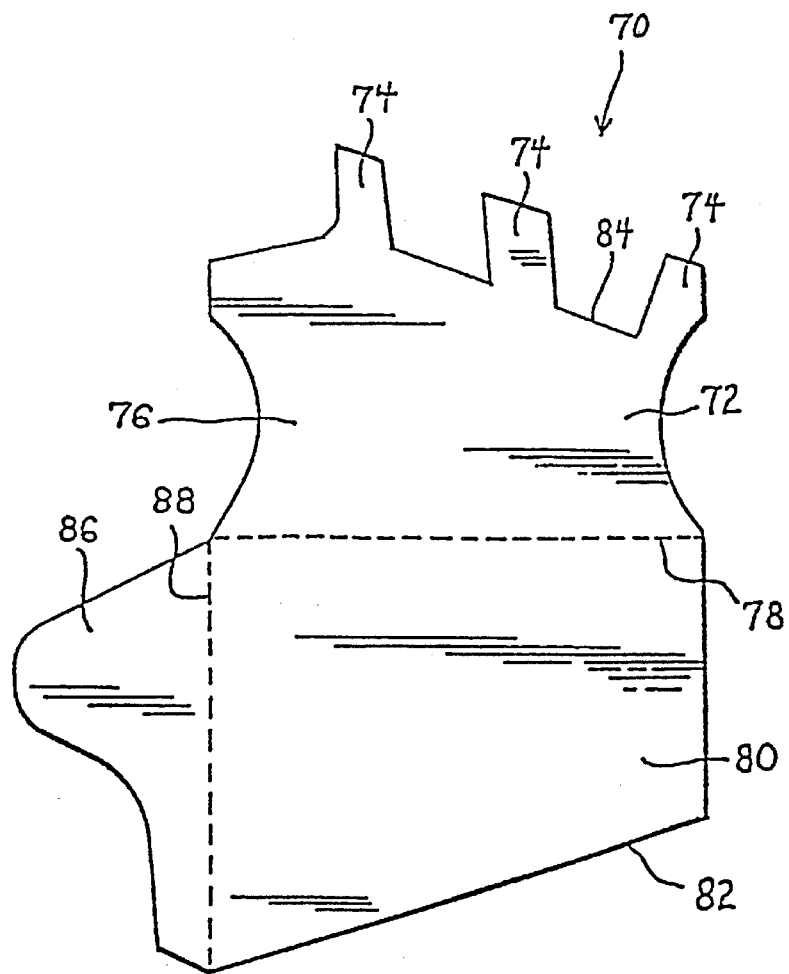
FIG. 7 illustrates a top plan view of a further embodiment of the needle shield of the present invention.

Turning now to FIG. 7, a further alternate embodiment of the needle shield is shown. Needle shield 70 is constructed of a sheet of fibrous material 72 having fork-like projections 74 which are spaced from each other along top edge 84. A score line 78 is provided which allows sheet 72 to be folded over on itself to define bottom sheet 76 and top sheet 80. A wing-like projection 86 is provided which is foldable about score line 88 which will be described below.

Figure 8:
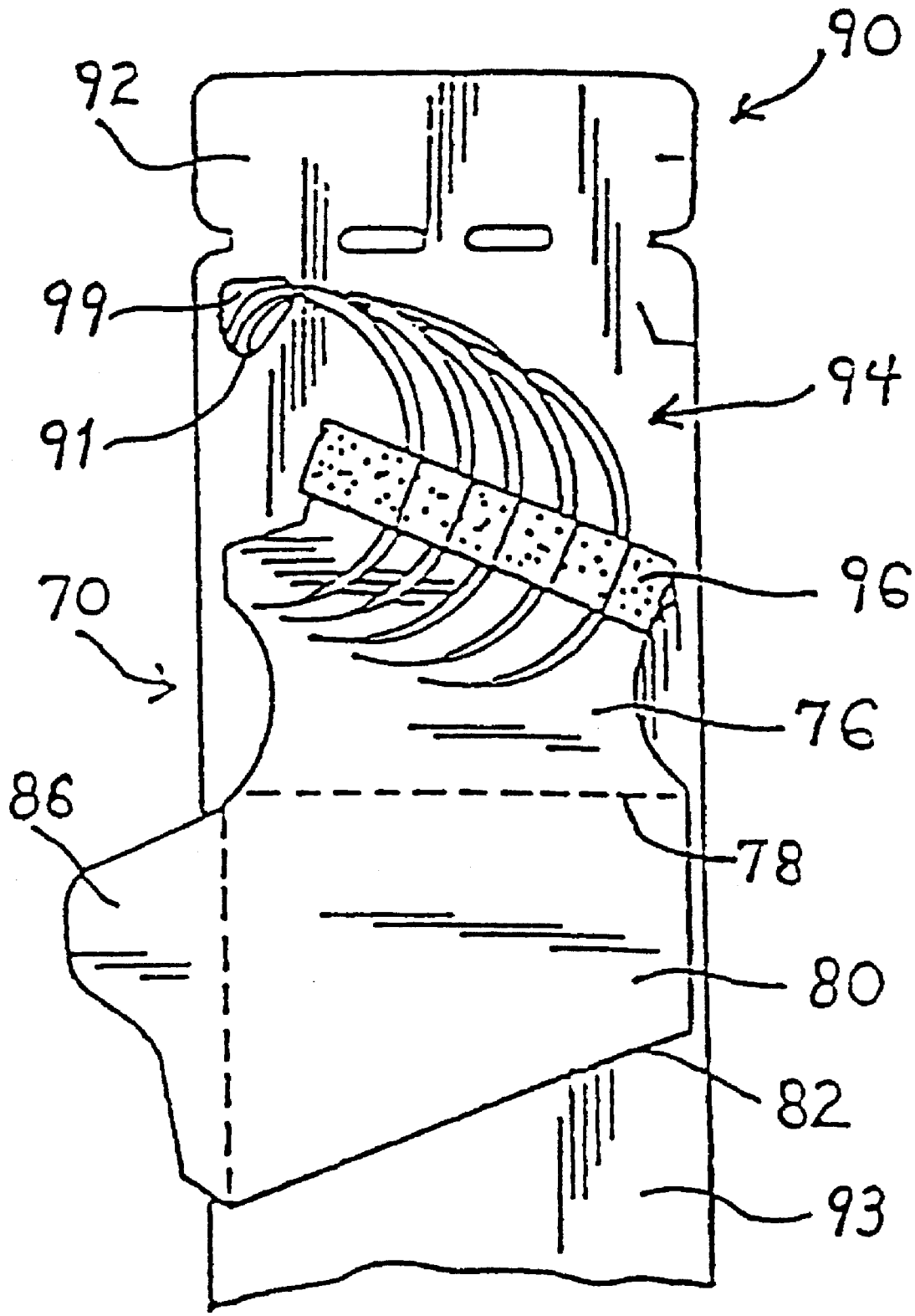
FIG. 8 illustrates the needle shield of FIG. 7 in position on a suture-needle retainer in the open position.

As best seen in FIG. 8, needle shield 70 is positioned on a suture-needle retainer 90 which is identical to retainer 32 described above and shown in FIG. 10. The shield 90 secures to cover panel 93 through the provision of an adhesive backed foam needle park 96. Foam needle park 96 secures needle shield 70 to cover panel 93 of retainer 90 in much the same manner as described above in reference to FIGS. 2 and 5. In this embodiment, upper edge 84 is positioned at an angle to score line 78, and needle park 96 is positioned along upper edge 84 to secure needle shield 70 through fork-like projections 74. After needle shield 70 is secured to retainer 90, needles 94, which are attached to the sutures positioned between cover panel 93 and bottom panel 99, and which extend through aperture 91, are secured in needle park 96 as shown.

Figure 9:
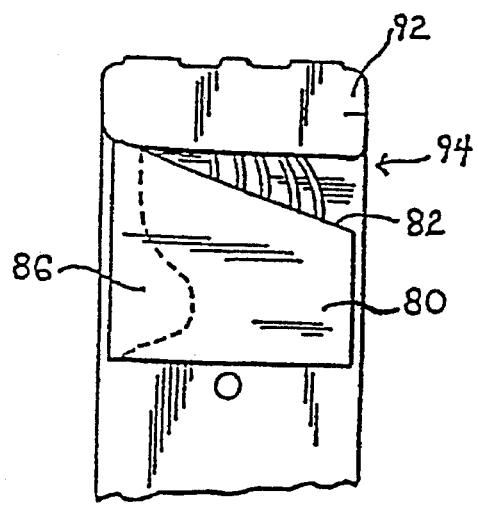
FIG. 9 illustrates the needle shield of FIG. 8 in position on a suture-needle retainer in the closed position.

In use, after sutures 94b are positioned in retainer 90, needles 94 are positioned in needle park 96 so that the tips of the needles are positioned on bottom sheet 76. Needle shield 70 is then folded on score line 78 so that the needle tips are positioned between bottom sheet 76 and top sheet 80. Edge 82 of top sheet 80 is angled relative to score line 78 so that when top sheet 80 is folded onto bottom sheet 76, edge 82 is aligned with the edge of foam needle park 96 as best seen in FIG. 9. At this point, wing-like projection 86 is folded about score line 88 and tucked under bottom sheet 76 to secure the needle shield about the needle. Flap 92 is then folded down onto the suture ends of the needles to secure the needles therein while providing a view of the needles as best seen in FIG. 9.

Figure 11:
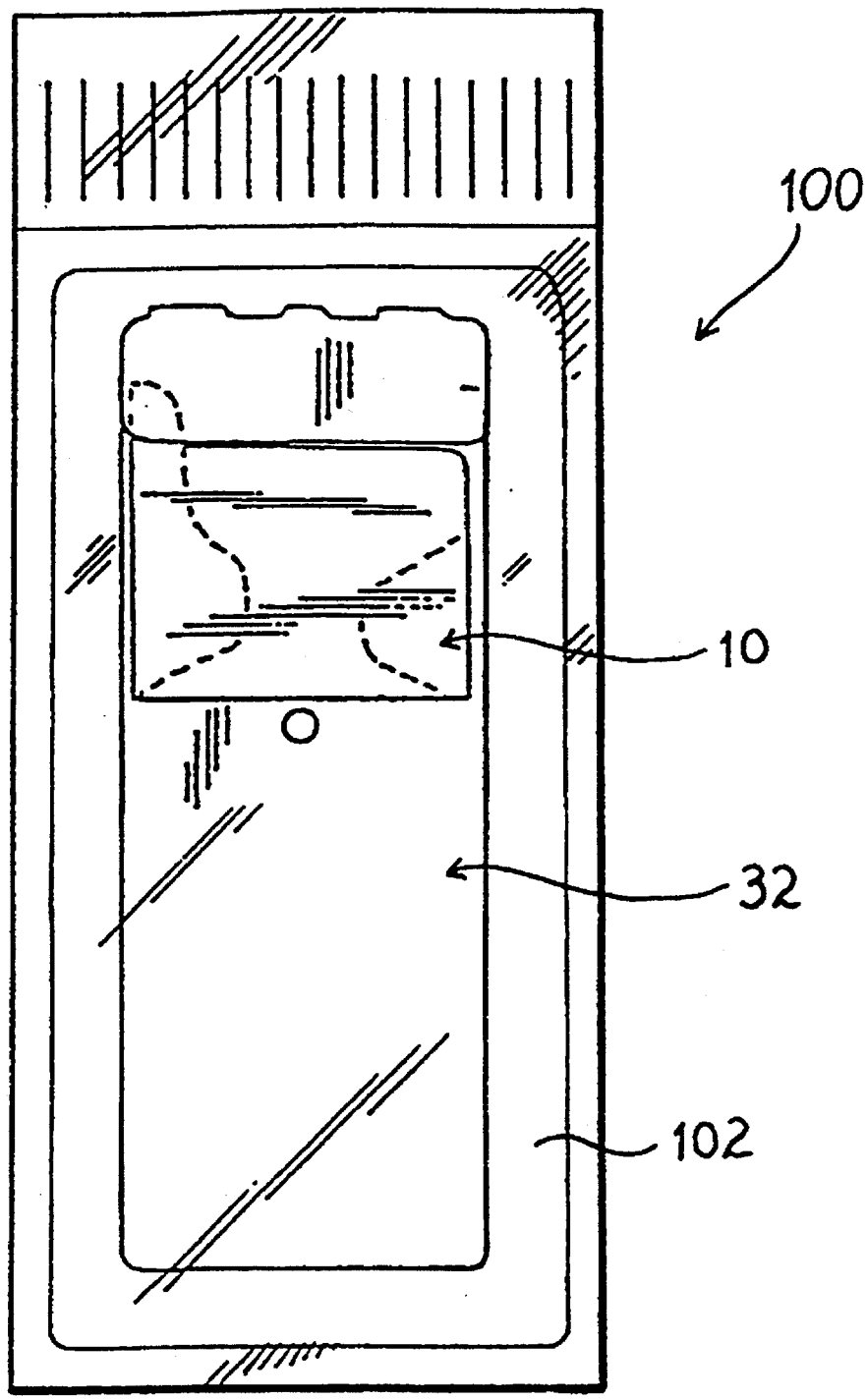
FIG. 11 illustrates the retainer and needle shield of FIG. 10 enclosed in an outer package.

Turning now to FIG. 11, retainer 32 having needle shield 10 positioned thereon is illustrated and is enclosed in outer package 100. Package 100 maintains sterility of the suture-needle assemblies packaged in retainer 32, and may comprise a so-called "breather pouch" as illustrated in FIG. 11. However, it is apparent that outer package 100 may comprise any end-use package known in the suture industry, including, but not limited to, plastic or metal foil pouches which maintain both sterility and prevent evaporation of conditioning fluid media packaged with the sutures.

The benefit of needle shield 10 of the present invention is clearly seen in FIG. 11. Without shield 10, the needle tips would be directly contacting the inner surface of top sheet 102 of package 100, which would increase the possibility of puncture of the sterile package 100. The needle shield 10 protects package 100 from the tips of the needles.

While the invention has been particularly shown and described with reference to the preferred embodiments, it will be understood by those skilled in the art that various modifications and changes in form and detail may be made therein without departing from the scope and spirit of the invention. Accordingly, modifications such as those listed above, but not limited thereto, are to be considered within the scope of the invention.

What is claimed is:

1. A method of loading a suture retainer comprising the steps of:

positioning at least one suture between a first panel and a second panel of a suture retainer, said suture having a needle secured to at least one end thereof, such that said needle is positioned outside said first and second panels, mounting a needle shield member to one of said first and second panels, positioning said needle on said needle shield member, and folding said needle shield member about said needle to enclose said needle therein.

2. A method according to claim 1, wherein said step of mounting said needle shield member to one of said panels comprises positioning an edge of said shield member between one of said panels and an adhesive-backed foam needle park.

3. A method according to claim 2, wherein said step of positioning said needle on said shield member comprises securing said needle in said needle park.

4. A method according to claim 1, further comprising the step of enclosing said loaded suture retainer in an outer envelope.

\* \* \* \* \*